United States Patent
Sugiyama et al.

(10) Patent No.: US 9,405,958 B2
(45) Date of Patent: Aug. 2, 2016

(54) CELL ANALYSIS METHOD, CELL ANALYSIS DEVICE, AND CELL ANALYSIS PROGRAM

(75) Inventors: Norikazu Sugiyama, Hamamatsu (JP); Tomochika Takeshima, Hamamatsu (JP); Kouichi Kaneko, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 103 days.

(21) Appl. No.: 14/113,934

(22) PCT Filed: Feb. 23, 2012

(86) PCT No.: PCT/JP2012/054457
§ 371 (c)(1),
(2), (4) Date: Nov. 14, 2013

(87) PCT Pub. No.: WO2012/147403
PCT Pub. Date: Nov. 1, 2012

(65) Prior Publication Data
US 2014/0064594 A1    Mar. 6, 2014

(30) Foreign Application Priority Data

Apr. 28, 2011  (JP) ................. 2011-101377

(51) Int. Cl.
*G06K 9/00* (2006.01)
*C12M 1/34* (2006.01)
(Continued)

(52) U.S. Cl.
CPC ........... *G06K 9/00147* (2013.01); *C12M 41/36* (2013.01); *G01N 33/5026* (2013.01); *G02B 21/14* (2013.01); *G06K 9/0014* (2013.01); *G06K 9/00134* (2013.01); *G01N 21/6458* (2013.01)

(58) Field of Classification Search
None
See application file for complete search history.

(56) References Cited

U.S. PATENT DOCUMENTS 5,843,780 A * 12/1998 Thomson .................. 435/363
2003/0179916 A1* 9/2003 Magnuson et al. ........... 382/128
(Continued)

FOREIGN PATENT DOCUMENTS

JP  2006-271210    10/2006
JP  2007-529747 A  10/2007
(Continued)

OTHER PUBLICATIONS

J. J Chan et al. "Label-Free Separation of Human Embryonic Stem Cells and Their Cardiac Derivatives Using Raman Spectroscopy", Analytical Chemistry, vol. 81, No. 4, Feb. 2009, p. 1324-1331.*
(Continued)

*Primary Examiner* — Utpal Shah
*Assistant Examiner* — Samah Beg
(74) *Attorney, Agent, or Firm* — Drinker Biddle & Reath LLP

(57) ABSTRACT

Provided is a cell analysis method in a cell analysis device D that uses an optical path length image of a cell colony formed of a large number of cells to analyze the cell colony, the method comprising: acquiring the optical path length image of the cell colony by an acquisition unit of the cell analysis device; extracting a circular shape corresponding to a cell nucleus of the cell in the acquired optical path length image by an extraction unit of the cell analysis device extracts; comparing an inner optical path length of the extracted circular shape and an outer optical path length of the extracted circular shape by a comparison unit of the cell analysis device extracts; and analyzing the cell colony based on the comparison result by analysis unit of the cell analysis device.

25 Claims, 15 Drawing Sheets
(1 of 15 Drawing Sheet(s) Filed in Color)

(51) Int. Cl.
*G02B 21/14* (2006.01)
*G01N 33/50* (2006.01)
*G01N 21/64* (2006.01)

(56) References Cited

U.S. PATENT DOCUMENTS

| | | | |
|---|---|---|---|
| 2005/0095708 A1* | 5/2005 | Pera et al. | 435/369 |
| 2005/0168808 A1* | 8/2005 | Ishiwata | G02B 21/361 359/368 |
| 2006/0039593 A1* | 2/2006 | Sammak et al. | 382/133 |
| 2008/0279441 A1* | 11/2008 | Matsuo | G01N 15/1475 382/133 |
| 2009/0086314 A1* | 4/2009 | Namba | G01N 21/6458 359/383 |
| 2009/0154788 A1* | 6/2009 | Maiya et al. | 382/133 |
| 2010/0172569 A1* | 7/2010 | Takagi | G01N 15/1475 382/133 |
| 2011/0002525 A1* | 1/2011 | Mimura | C12M 23/48 382/133 |
| 2011/0019897 A1* | 1/2011 | Takagi et al. | 382/133 |
| 2011/0019898 A1* | 1/2011 | Takagi et al. | 382/133 |
| 2011/0188728 A1* | 8/2011 | Sammak et al. | 382/133 |
| 2012/0106822 A1* | 5/2012 | Mimura | C12M 41/46 382/133 |
| 2012/0122143 A1* | 5/2012 | Mimura | C12M 41/14 435/29 |
| 2012/0142095 A1* | 6/2012 | Yano | C12M 41/46 435/366 |
| 2012/0315620 A1* | 12/2012 | Watakabe et al. | 435/3 |
| 2013/0130228 A1* | 5/2013 | Watakabe et al. | 435/3 |
| 2013/0130307 A1* | 5/2013 | Sugiyama et al. | 435/34 |
| 2013/0236961 A1* | 9/2013 | Amit et al. | 435/366 |

FOREIGN PATENT DOCUMENTS

| | | | |
|---|---|---|---|
| JP | 2008-212017 A | | 9/2008 |
| JP | 2008212017 | * | 9/2008 |
| JP | 2009-542237 A | | 12/2009 |
| JP | 2011-024485 A | | 2/2011 |
| WO | WO2011043077 | * | 4/2011 |

OTHER PUBLICATIONS

A. Downes et al. "Optical Spectroscopy for NoninvasiveMonitoring of Stem Cell Differentiation", Journal of Biomedicine and Biotechnology, 2010.*

Yamauchi, Toyohiko, et al., "Label-free Classification of Cell Types by Imaging of Cell Membrane Fluctuations Using Low-Coherent Full-Field Quantitative Phase Microscopy," Proceedings of Spie, vol. 7570, Jan. 25, 2010, pp. 1-8.

Wang, Pin, et al., "Spatial-Domain Low-Coherence Quantitative Phase Microscopy for Cancer Diagnosis," Optics Letters, Optical Society of America, U.S., vol. 35, No. 17, Sep. 1, 2010, pp. 2840-2842.

Niyom Lue et al., "Synthetic aperture tomographic phase microscopy for 3D imaging of live cells in translational motion," Optics Express, Sep. 29, 2008, pp. 16240-16246, vol. 16, No. 20.

* cited by examiner (B)

(A)

CELL ANALYSIS METHOD, CELL ANALYSIS DEVICE, AND CELL ANALYSIS PROGRAM

TECHNICAL FIELD

The present invention relates to a cell analysis method, a cell analysis device, and a cell analysis program.

BACKGROUND ART

Stem cells such as ES cells and iPS cells, which are derived from a human, have ability to differentiate into various kinds of cells and may be applied to large-scale efficacy evaluation or medical treatment using human cells, such as resolution of disease or, drug discovery screening, a toxicity test, and regenerative medicine, which have been difficult to achieve so far, and thus have attracted attention. It is considered that the differentiation efficiency when differentiation is induced from these stem cells into target cells greatly depends on the state of stem cells which are a starting material. That is, when stem cells do not maintain an undifferentiated state while maintaining pluripotency, the efficiency of differentiation induction is reduced. For that reason, for an industrial application of these stem cells, it is extremely important to manage the quality of stem cells in a process of culturing stem cells, and it is necessary to monitor stem cells and determine the state thereof. Further, in the management process, it is necessary to non-invasively determine the cells while being cultured. In addition, these stem cells form a colony (a cell population formed by several thousand to several tens of thousands of cells), and thus there is a need for a technology for determining the quality in a state of colony. The colony is not always formed by cells with uniform quality, and the cell characteristics vary from site to site. For that reason, it is preferred to obtain information, such as a map, which is capable of determining the distribution of the cell state inside the colony by using, as an index, the state of individual cells constituting a colony.

Patent Literature 1 discloses a cell-image analyzing apparatus that analyzes a cell image, determines, to be specific, in a region in which regions forming a colony and regions not forming a colony coexist, the regions forming a colony, and acquires information such as position and size of the regions forming a colony. In particular, single-cell regions forming a colony have a shape approximate to a circle, and thus a colony region is distinguished from a non-colony region in accordance with circularity (a value which is small when the shape is a circle, and increases when the shape deviates from the circle).

In an apparatus for determining a cell state which is described in Patent Literature 2, a device for determining an active state of floating cells first acquires an image of floating cells from viewpoint that the better the cell state is, the more approximate to a circle the floating cells are, and the worse the cell state is, the stronger the ellipticity is or the more distorted the shape becomes. Next, a contour of floating cells in the acquired phase image is extracted, and it is determined how approximate to a circle the extracted contour of floating cells is.

In a device for evaluating a culture solution, which is described in Patent Literature 3, a living cell and a dead cell are distinguished by comparing the intensities of light at the inner side of a cell and the edge of the cell using the polarization characteristics of cells. In particular, it is described that in a living cell, the inner side of the cell is dark and the outer side of the cell is bright, and it is also described that it is possible to acquire an image having a high contrast when using a phase contrast microscope.

CITATION LIST

Patent Literature

Patent Literature 1: Japanese Patent Application Laid-Open No. 2011-24485
Patent Literature 2: Japanese Patent Application Laid-Open No. 2008-212017
Patent Literature 3: Japanese Patent Application National Publication No. 2003-529747

SUMMARY OF INVENTION

Technical Problem

In a method of visually observing and determining the shape of a cell or a colony using an optical microscope, the determination result is likely to depend on an observer's subjective view or experience. Furthermore, the method may be an obstacle to mass culture. Further, since the number of constituent cells is large, it is much more difficult to observe and determine the distribution of cells within a colony as compared with the visual observation of a single cell. Accordingly, it is thought that there is a need in the art for a method, a device, and a program for determining a state of a cell colony, which are quantitative and may be automated.

In the examples described in the above-described Patent Literatures 1 and 2, a circular shape is extracted in an acquired cell image, and a cell is evaluated in accordance with the circularity, area, circumference, and the like of the extracted circle. However, there is a case where cells with poor quality also have a circular shape, and thus it is not possible to accurately evaluate and identify whether cells forming a colony are cells with good quality by the above method.

Further, in the example described in the above-described Patent Literature 3, the inner side of a cell is compared with edge of the cell. However, in a colony, a plurality of cells aggregates densely and there are many cases where cells are in contact with each other, and thus it is not easy to accurately extract an edge of a cell. Accordingly, when an error occurs in the extraction of the edge of the cell, the result of determining the cell is also adversely affected.

Therefore, the present invention has been made in consideration of the above circumstances, and an object of the present invention is to provide a method, a device, and a program which determine a state of a cell colony and which are quantitative and automated and with high accuracy.

Solution to Problem

In order to solve the above problems, the cell analysis method of the present invention is a cell analysis method in a cell analysis device that uses an optical path length image of a cell colony formed of a large number of cells to analyze the cell colony, including: acquiring the optical path length image of the cell colony by an acquisition unit of the cell analysis device; extracting a circular shape corresponding to a cell nucleus of the cell in the acquired optical path length image by an extraction unit of the cell analysis device extracts; comparing an inner optical path length of the extracted circular shape and an outer optical path length of the extracted circular shape by a comparison unit of the cell analysis device extracts; and analyzing the cell colony based on the comparison result by analysis unit of the cell analysis device.

Further, the cell analysis device of the present invention is a cell analysis device that uses an optical path length image of a cell colony formed of a large number of cells to analyze the cell colony, including: acquisition unit configured to acquire the optical path length image of the cell colony; extraction unit configured to extract a circular shape corresponding to a cell nucleus of the cell in the acquired optical path length image; comparison unit configured to compare an inner optical path length of the extracted circular shape and an outer optical path length of the extracted circular shape; and analysis unit configured to analyze the cell colony based on the comparison result.

In addition, the cell analysis program of the present invention causes a computer to function as; in a cell analysis device that uses an optical path length image of a cell colony formed of a large number of cells to analyze the cell colony, acquisition unit configured to acquire the optical path length image of the cell colony; extraction unit configured to extract a circular shape corresponding to a cell nucleus of the cell in the acquired optical path length image; comparison unit configured to compare an inner optical path length of the extracted circular shape and an outer optical path length of the extracted circular shape; and analysis unit configured to analyze the cell colony based on the comparison result.

According to the cell analysis method, the cell analysis apparatus, and the cell analysis program of the present invention, it is possible to analyze a cell colony with high accuracy by a quantitative and automated technique. That is, it is possible to analyze a cell colony with high accuracy by a quantitative and automated technique, by all including extracting a circular shape corresponding to a cell nucleus and comparing an inner optical path length of the extracted circular shape and an outer optical path length of the extracted circular shape. By focusing on a difference between the inner and outer optical path lengths of the cell nucleus, that is, a difference between the optical path length in the cell nucleus and the optical path length in the cytoplasm around the cell nucleus, it is possible to use specific information of a cell with good quality for analysis of a cell colony, thereby analyzing a cell colony by a quantitative and automated technique. Further, it is possible to compensate for an appropriate analysis which was impossible with only extraction of a circular shape by focusing on not only shape information that the form is round, but also the quantitative difference in the optical path length, thereby realizing an analysis with high accuracy.

In addition, in the above-described Patent Literature 3, since the inner brightness of a cell is compared with the outer brightness thereof, it is necessary to exactly extract the contour of the cell, but when cells forming a cell colony are adjacent to each other, a boundary between the cells is not clear, and thus it cannot be said that the contour of the cell may be extracted accurately. Meanwhile, the present invention is different from Patent Literature 3 in that the inner and outer optical path lengths of the cell nucleus are compared with each other. Although a cell colony is formed, in a cell in good condition, the boundary of the cell nucleus may be clearly distinguished by a difference in refractive index between the nucleus and the cytoplasm thereof, and thus the inner and outer sides of the cell nucleus may be exactly distinguished. Therefore, according to the present invention, it is possible to analyze a cell colony with high accuracy.

As described above, by analyzing a state of cell colony with high accuracy by the quantitative and automated technique, evaluation by experience of an examiner until now becomes numerical values, which may be objectively compared, even though the evaluation may be performed by anybody, and thus it is possible to exclude ambiguous factors such as a subjective view of an examiner, a physical condition thereof, and variability among examiners. This makes it possible to uniformly analyze a cell colony based on predetermined determination criteria that do not depend on the skill of the examiner. Further, it is possible to alleviate the physical pain of the examiner who observes and determines a large number of cells and cell colonies with naked eyes. In addition, for example, by applying stepwise numerical values, it is possible to understand a temporal change in state, and in this case, for example, after the initiation of culture, it is possible to determine the sign and the like that the state deteriorates early. For that reason, it is possible to increase an opportunity of recovery before a state deteriorates, improve the efficiency percentage in the entire process, and avoid wasting culture materials, thereby leading to a reduction in production costs. In addition, it is possible to easily apply the same determination criteria to a process of another producer, and provide cells with common quality among different producers.

Further, in the present invention, in the comparing and the analyzing, when the outer optical path length of the circular shape is greater than the inner optical path length of the circular shape, the cell may be determined as a cell with good quality.

According to the present invention, a specific method for determining a cell with good quality is provided. The determination method according to the present invention is based on the following considerations by the inventors. That is, from the experimental results by the inventors, it has been derived that only in a cell with good quality, a shape of a cell nucleus is a circular shape and an inner optical path length of the cell nucleus is smaller than an outer optical path length of the cell nucleus. Meanwhile, it has been derived that in a cell with poor quality, a shape of a cell nucleus is not a circular shape, or an inner optical path length of the cell nucleus is equal to or greater than an outer optical path length of the cell nucleus even though the shape of the cell nucleus is a circular shape. Therefore, it is possible to determine that a cell is a cell with good quality when an outer optical path length of a cell nucleus of the cell is greater than an inner optical path length of the cell nucleus by comparing the difference between the inner and outer optical path lengths thereof.

Further, in the present invention, in the analyzing, when the number of cells per unit area, which are determined as the cell with good quality, is equal to or greater than a threshold, the cell colony may be determined as a cell colony with good quality.

According to the present invention, a specific method for distinguishing between a cell colony with good quality and a cell colony with no good quality is provided. This is consistent with the purpose of industrial applications for quality management of a cell colony unit. It is because throughput does not increase by individually evaluating cells. Further, the present method is a method based on characteristics of a cell colony. That is, a cell colony is formed through division and proliferation of cells, and thus there is a tendency that there are a large number of cells with good quality around a cell with good quality, and there are a large number of cells with poor quality around a cell with poor quality. From this point of view, it can be said that the number of cells per unit area, which are determined as a cell with good quality, is appropriate as a determination criterion for distinguishing between a cell colony with good quality and a cell colony with no good quality.

Further, the present invention may further include specifying and displaying a region of the cell colony with good quality by display unit of the cell analysis device.

According to the present invention, a specific method for a user of the present invention so as to easily confirm the analysis result of a cell colony according to the present invention is provided.

Further, in the present invention, the optical path length image may be a quantitative optical path length image.

According to the present invention, it is possible to readily compare an inner optical path length and an outer optical path length of a circular shape by a quantitative optical path length image.

Further, in the present invention, the circular shape may be a true circular shape.

According to the present invention, a primary determination criterion of a cell with good quality is provided. Depending on the accuracy or purpose of the cell analysis, it is possible to adopt as the determination criterion that the circular shape is a true circular shape.

Further, in the present invention, the true circular shape may be a true circular shape having a predetermined diameter range.

According to the present invention, a primary determination criterion of a cell with good quality is provided. Depending on the accuracy or purpose of the cell analysis, it is possible to adopt as the determination criterion that the circular shape is a true circular shape having a predetermined diameter range.

Further, in the present invention, the circular shape may be an elliptical shape.

According to the present invention, a primary determination criterion of a cell with good quality is provided. Depending on the accuracy or purpose of the cell analysis, it is possible to adopt as the determination criterion that the circular shape is an elliptical shape.

Further, in the present invention, the cell may be a stem cell.

The present invention may be utilized in industrial applications of stem cells including iPS cells and ES cells. For example, when the present invention is applied to a device of culturing stem cells, and the like, it is possible to determine stem cells or stem cell colonies, which are being cultured, by a quantitative and automated technique and with higher accuracy, thereby enabling labor saving and mass production.

Advantageous Effects of Invention

According to the present invention, it is possible to provide a cell analysis method, a cell analysis device, and a cell analysis program which may determine a state of a cell colony and which are quantitative and automated and with higher accuracy.

BRIEF DESCRIPTION OF DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Figure 1:
FIG. 1 is an image of a quantitative phase microscope illustrating an example of stem cells with good quality and stem cells with poor quality.
Figure 1:
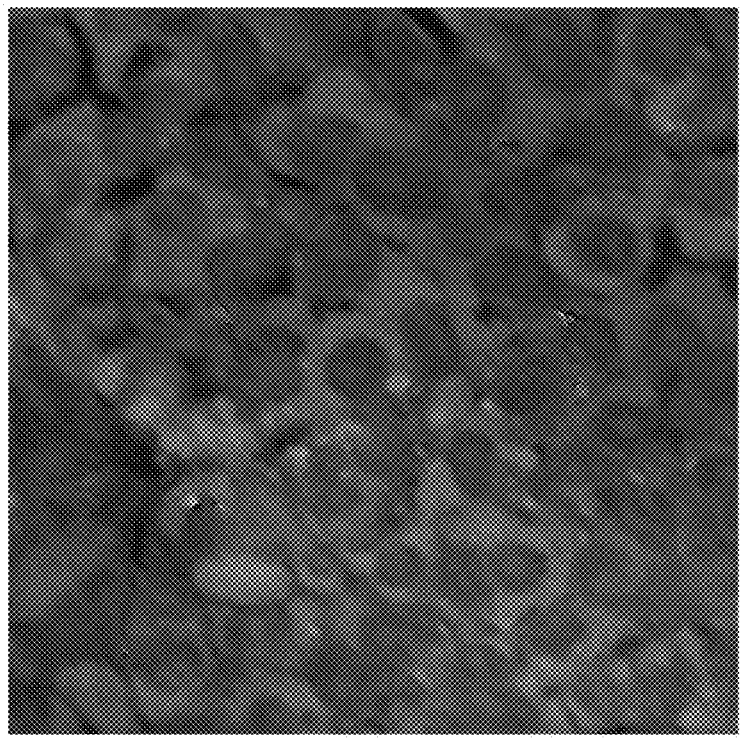

Hereinafter, exemplary embodiments of a cell analysis method, a cell analysis device, and a cell analysis program according to the present invention will be described in detail with reference to the accompanying drawings. Further, in describing the drawings, the same reference numerals are given to the same elements, and overlapping description will be omitted.

(Basic Concept)

First, the basic concept of the present invention will be described. FIG. 1 is an image of a quantitative phase microscope illustrating an example of stem cells with good quality (FIG. 1(A)) and stem cells with poor quality (FIG. 1(B)), and the object of the present invention is to provide a method, a device, and a program which determine cells with good quality and cells with poor quality to be quantitative and be automated and with higher accuracy, thereby determining a state of a cell colony.

Figure 2:
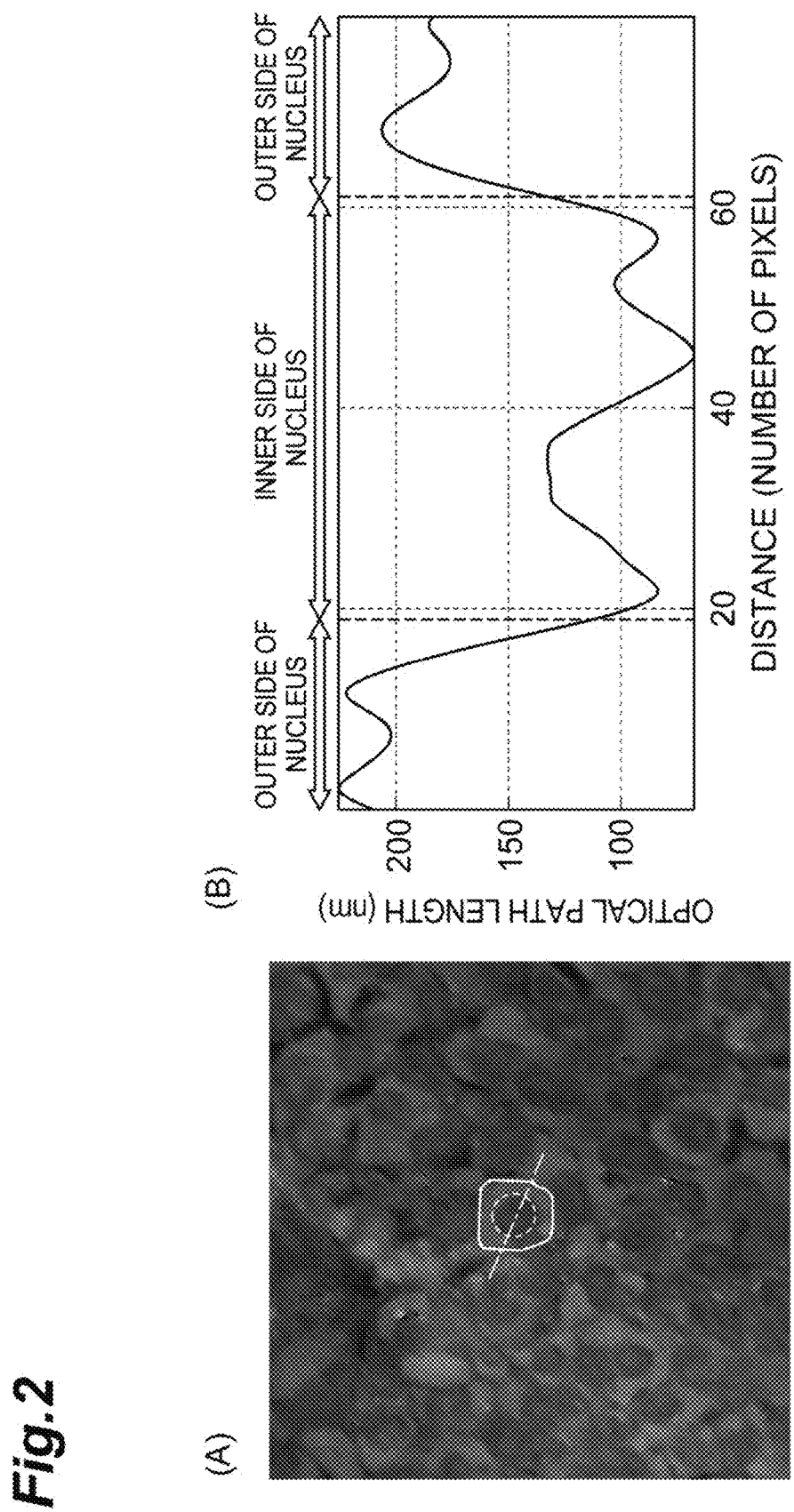
FIG. 2 is a view for explaining the characteristics of stem cells with good quality.

FIG. 2 is a view for explaining the characteristics of the stem cell with good quality as illustrated in FIG. 1(A). In FIG. 2(A), a solid line indicates the contour of the stem cell, a broken line indicates the contour of the nucleus of the stem cell, and a dashed-dotted line indicates a line profile. As illustrated in FIG. 2(A), in the stem cell with good quality, the nucleus thereof has a strong tendency to form a true circle (see the broken line). FIG. 2(B) is a view illustrating an optical path length by allowing the line profile indicated by a dashed-dotted line in FIG. 2(A) to correspond to a horizontal axis. As illustrated in FIG. 2(B), it can be seen that in the stem cell with good quality, an inner optical path length of the cell nucleus is smaller than an outer optical path length of the cell nucleus. Further, in the embodiment, "optical path length" may be understood as "phase difference" or "optical thickness", but for convenience of explanation, the terms will be unified and described as the "optical path length" in the following.

Figure 3:
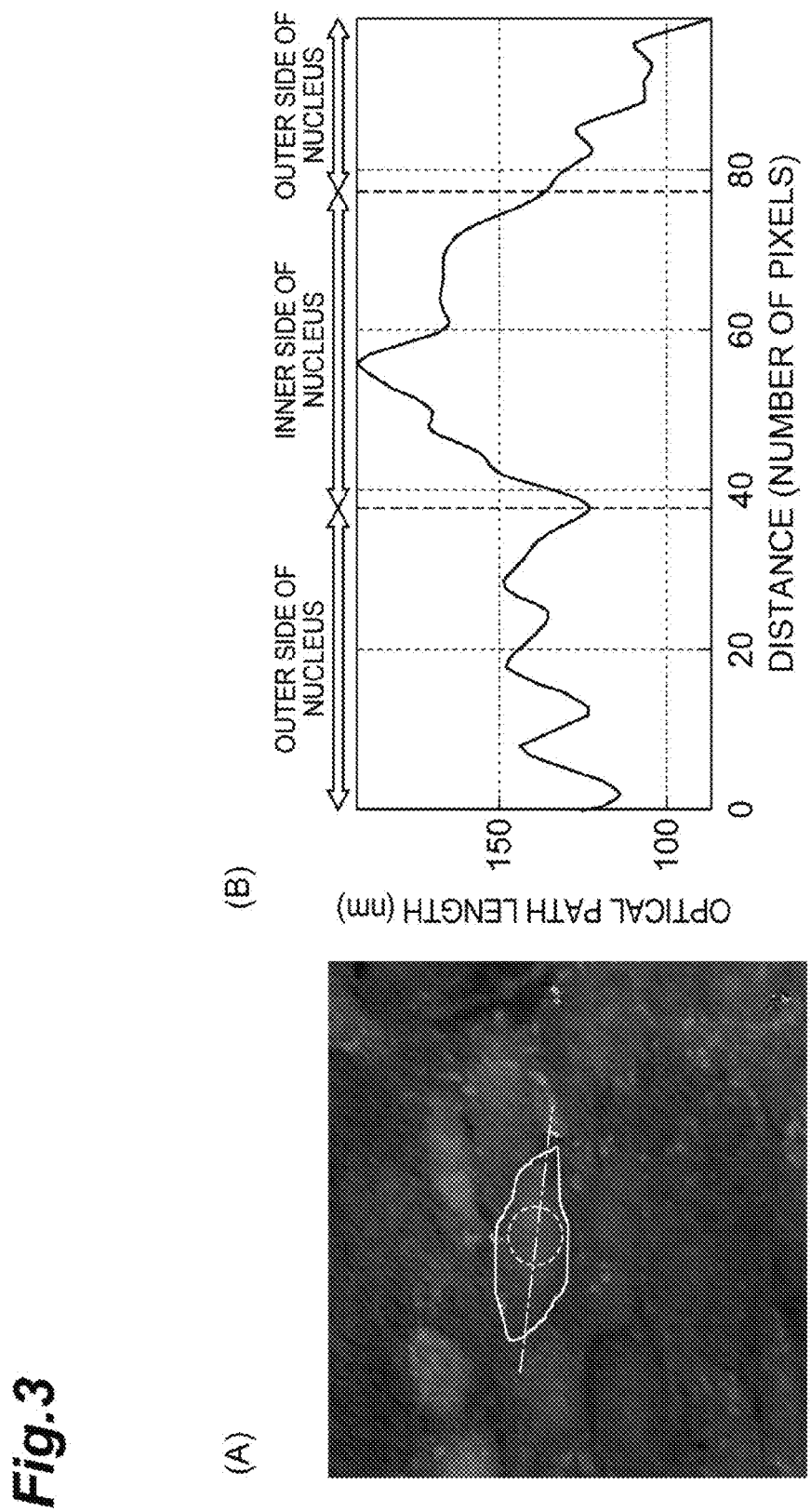
FIG. 3 is a view for explaining the characteristics of stem cells with poor quality.

FIG. 3 is a view for explaining the characteristics of the stem cell with poor quality as illustrated in FIG. 1(B). In FIG. 3(A), a solid line indicates the contour of the stem cell, a broken line indicates the contour of the nucleus of the stem cell, and a dashed-dotted line indicates a line profile. As illustrated in FIG. 3(A), there is a case where, even in the stem cell with poor quality, the nucleus thereof forms a true circle (see the broken line). FIG. 3(B) is a view illustrating an optical path length by allowing the line profile indicated by a dashed line in FIG. 3(A) to correspond to a horizontal axis. As illustrated in FIG. 3(B), it can be seen that, even when in the stem cell with poor quality, the cell nucleus thereof forms, for example, a true circle, an inner optical path length of the cell nucleus is not smaller than an outer optical path length of the cell nucleus.

As seen in FIGS. 2 and 3, the critical difference between the stem cell with good quality and the stem cell with poor quality is in the inner and outer optical path lengths of the cell nucleus, not whether the cell nucleus is a true circle or not. Further, although not illustrated, when a cell nucleus of a stem cell is not a true circle, the stem cell is more likely to be a stem cell with poor quality. Accordingly, in the present invention, whether a cell nucleus is an exact circular shape or not is determined and inner and outer optical path lengths of the cell nucleus are compared, thereby realizing providing a method, a device, and a program which determine cells with good quality and cells with poor quality to be quantitative and automated and with high accuracy so as to determine a state of a colony, which is an object of the present invention.

Figure 4:
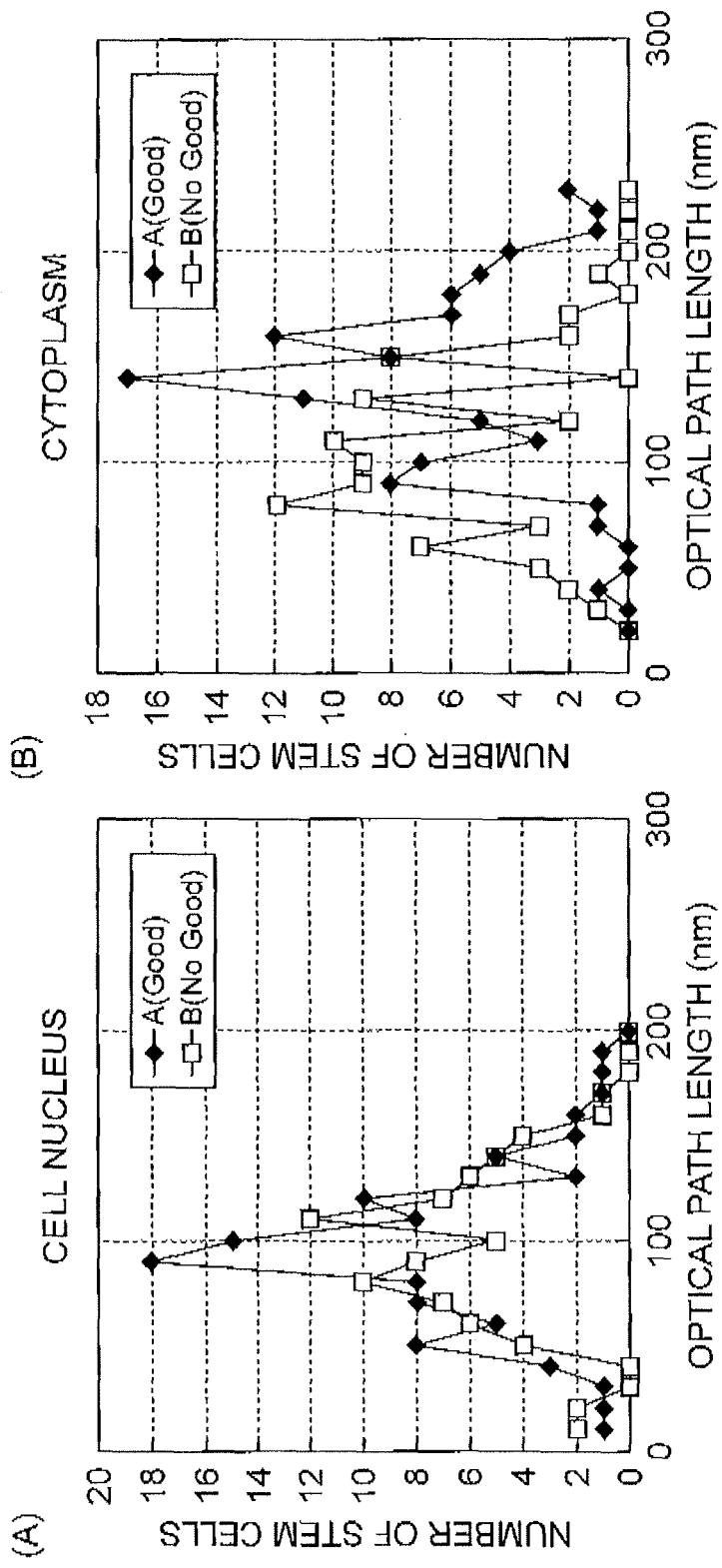
FIG. 4(A) is a view illustrating the results of measuring an optical path length of cell nucleus.
FIG. 4(B) is a view illustrating the results of measuring an optical path length of cytoplasm (outer side of the cell nucleus).
Figure 5:
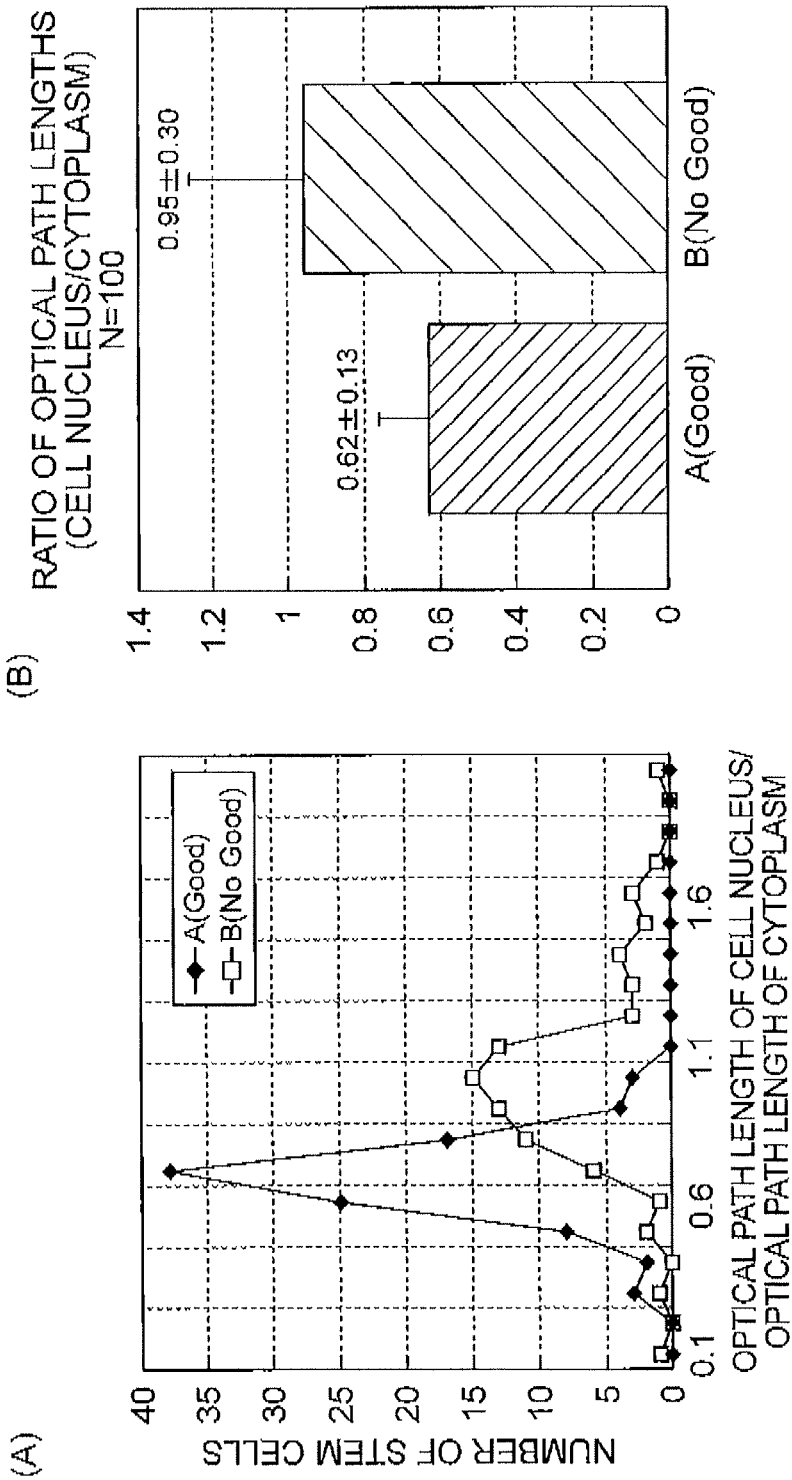
FIG. 5 is a view illustrating, based on the measurement results of the optical path length in FIG. 4, a ratio of the optical path lengths of the cell nucleus and the cytoplasm ((A) in FIG. 5) and an average ratio of the optical path lengths ((B) in FIG. 5) when the total number of stem cells is set to 100.

FIGS. 4 and 5 are views for further explaining that the critical difference between a stem cell with good quality and a stem cell with poor quality is in the inner and outer optical path lengths of the cell nucleus. FIG. 4(A) illustrates the results of measuring the optical path length of the cell nucleus, graph A shows the optical path lengths of the cell nuclei of stem cells with good quality, and graph B shows the optical path lengths of the cell nuclei of stem cells with poor quality. Further, FIG. 4(B) illustrates the results of measuring the optical path length of cytoplasm (outer side of the cell nucleus), graph A shows the optical path length of the cytoplasm of a stem cell with good quality, and graph B shows the optical path length of the cytoplasm of stem cells with poor quality. In addition, FIGS. 5(A) and (B) illustrate, based on the measurement results of the optical path length in FIG. 4, a ratio of the optical path lengths of the cell nucleus and the cytoplasm (FIG. 5(A)) and an average ratio of the optical path lengths when the total number of stem cells is set to 100 (FIG. 5(B)). In FIG. 5(A), graph A shows the case of stem cells with good quality and graph B shows the case of stem cells with poor quality. Furthermore, in FIG. 5(B), the left bar (symbol A) indicates the case of stem cells with good quality and the right bar (symbol B) indicates the case of stem cells with poor quality. As illustrated in these drawings, there is a clear difference in the optical path length between the stem cell with good quality and the stem cell with poor quality, and based on this, it is possible to determine stem cells with good quality and stem cells with poor quality to be quantitative and automated and with higher accuracy.

(Configuration of Cell Analysis System 1)

Figure 6:
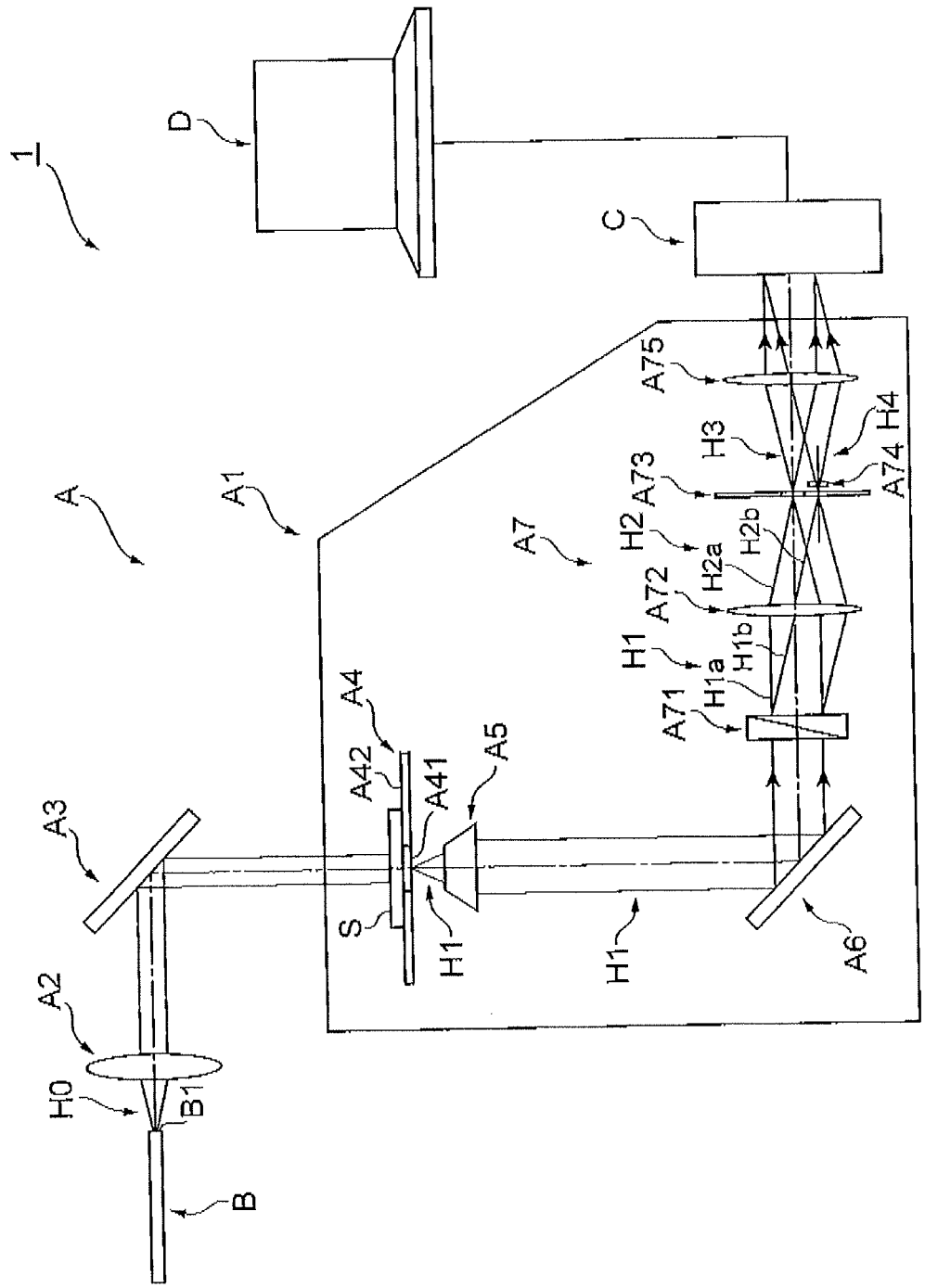
FIG. 6 is a configuration diagram of a cell analysis system 1.
Figure 7:
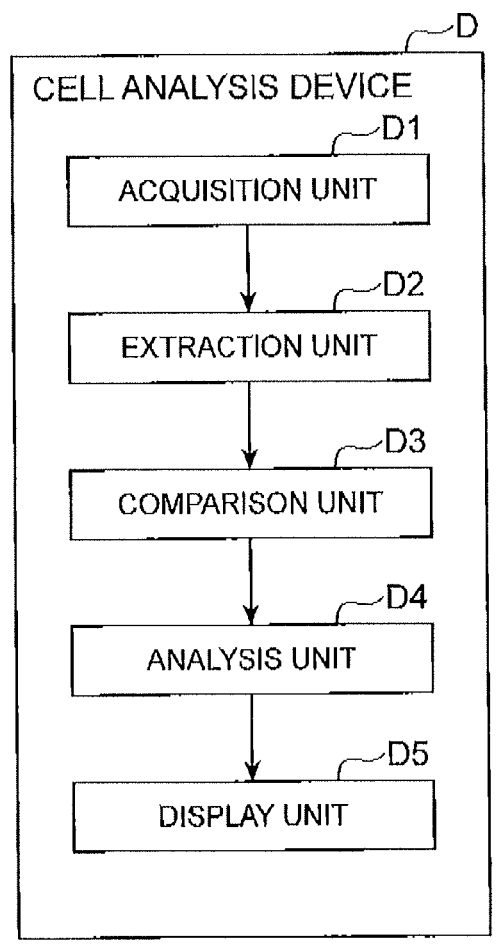
FIG. 7 is a schematic view illustrating a functional configuration of a cell analysis device D.
Figure 8:
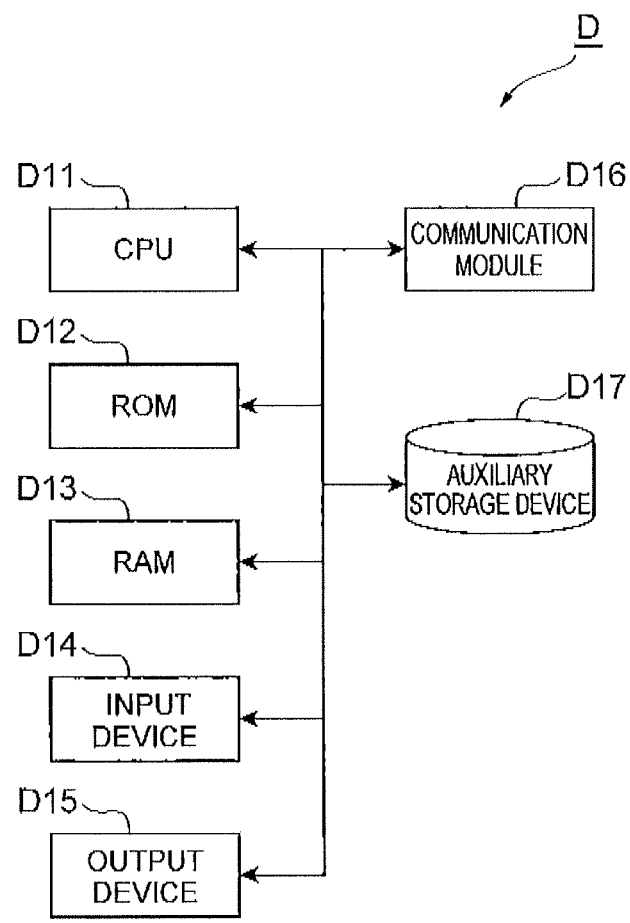
FIG. 8 is a schematic view illustrating a hardware configuration of the cell analysis device D.

Hereinafter, a configuration of a cell analysis system 1 according to an embodiment of the present invention will be described. The cell analysis system 1 analyzes a cell colony using an optical path length image of the cell colony formed by a large number of cells. FIG. 6 is a configuration diagram of the cell analysis system 1, FIG. 7 is a schematic view illustrating a functional configuration of the cell analysis device D, and FIG. 8 is a schematic view illustrating a hardware configuration of the cell analysis device D.

As illustrated in FIG. 6, the cell analysis system 1 is mainly constituted by a quantitative phase microscopy A and the cell analysis device D. The quantitative phase microscope A includes a stage A4 that supports a measurement sample S, an objective lens A5, a reflection unit A6, and a microscope main body A1 including an optical interference unit A7. The light incidence side of the microscope main body A1 includes a lens A2 which is made to face an emission side end face B1 of an optical fiber B that guides an irradiation light H0 (laser beam) from a light emitting unit which is not illustrated, and a reflection unit A3 that reflects the light H0 passing through the lens A2. Meanwhile, the emission side of light includes an imaging device C such as a CCD camera which images interference fringes (not illustrated, hereinafter the same) generated by the optical interference unit A7, and a cell analysis device D which is connected to the imaging device C and analyzes the interference fringes.

[Configuration of Quantitative Phase Microscope A]

The stage A4 includes, for example, a light transmission unit A41 capable of transmitting light in the center thereof, and has an approximately plate shape having a mounting surface A42 capable of mounting the measurement sample S on the upward surface thereof. By irradiating light from above while the measurement sample S is mounted on the mounting surface A42, light (measured light H1) passing through the measurement sample S passes through the light transmission unit A41 to face toward the objective lens A5. Further, the light transmission unit A41 may be formed by, for example, a member, such as glass, that may transmit light, or may be a simple hole. The objective lens A5 enlarges, based on, for example, the operation of an operation unit (not illustrated), the measured light H1, which is incident, at a predetermined magnification ratio according to the operation to emit the enlarged light as parallel light (measured light H1). The reflection unit A6 is, for example, an all-reflective mirror, and allows the measured light H1 from the objective lens A5 to be totally reflected and introduced into the optical interference unit A7. The optical interference unit A7 includes a light split element A71 which splits the measured light H1 into two lights H1a and H1b, a collective lens A72 which converts the measured light H1 (H1a and H1b) emitted by the light split element A71 into convergent light 112 (H1a and H2b), a spatial filter A73 disposed at a convergence position of the convergent light H2, and a complex lens A75 which produces interference fringes by superimposing object light H3 and reference light H4 which have passed through the spatial filter A73. Here, the light split element A71 is configured by using a diffraction grating. Further, the light split element A71 may be a polarizing beam splitter that splits a beam of light into two beams the polarization directions of which are different from each other. In this case, the optical interference unit A7 includes the light split element A71 which splits the measured light H1 into the two lights H1a and H1b the polarization directions of which are different from each other, the collective lens A72 which converts the measured light H1 into the convergent light H2 (H2a and H2b), the spatial filter A73 disposed at a convergence position of the convergent light H2, object light H3 and reference light H4 which have passed through the spatial filter A73, a half-wave plate A74 disposed at the emission side of the spatial filter A73, and the complex lens A75 which produces interference fringes by superimposing the object light H3 and the reference light H4 the polarization directions of which are aligned by the half-wave plate A74. Alternatively, the polarization directions of the object light H3 and the reference light H4 may be aligned by disposing a polarizer in place of the half-wave plate A74 that is disposed at the emission side of the spatial filter A73. Further, the configuration of the quantitative phase microscope A described above is only an example, and the present invention is not limited to the configuration example.

[Configuration of Cell Analysis Device D]

Next, the description of the cell analysis device D will be described. As illustrated in FIG. 8, the cell analysis device d is physically configured as a general computer system including a main storage device such as a CPU D11, an ROM D12, and an RAM D13, an input device D14 such as a keyboard and a mouse, an output device D15 such as a display, a communication module D16 such as a network card which transmits and receives data to and from other devices such as an imaging device C, and an auxiliary storage device D17 such as a hard disk. Each function of the cell analysis device D to be described below is implemented by reading predetermined computer software in hardware such as the CPU D11, the ROM D12, and the RAM D13 so as to operate the input device D14, the output device D15, and the communication module D16 under the control of the CPU D11, and read and write data in the main storage devices D12 and D13, or the auxiliary storage device D17.

As illustrated in FIG. 7, as functional components, the cell analysis device D includes an acquisition unit D1 (corresponding to "acquisition unit" and "acquiring" in the claims), an extraction unit D2 (corresponding to "extraction unit" and "extracting" in the claims), a comparison unit D3 (corresponding to "comparison unit" and "comparing" in the claims), an analysis unit D4 (corresponding to "analysis unit" and "analyzing" in the claims), and a display unit D5 (corresponding to "display unit" and "displaying" in the claims).

The acquisition unit D1 acquires an optical path length image of a cell colony from the imaging device C. The extraction unit D2 extracts a circular shape corresponding to a cell nucleus of a cell in the acquired optical path length image. The comparison unit D3 compares an inner optical path length of the extracted circular shape and an outer optical path length of the extracted circular shape. The analysis unit D4 analyzes the cell and the cell colony based on the comparison result. When the outer optical path length of the circular shape is greater than the inner optical path length of the circular shape, the comparison unit D3 and the analysis unit D4 determine that the cell is a cell with good quality. When the number of the cells per unit area, which are determined as a cell with good quality, is equal to or greater than a threshold, the analysis unit D4 determines that the cell colony is a cell colony with good quality. The display unit D5 specifies and displays a region included in a cell colony the quality of which is determined as being good.

(Operation of Cell Analysis System 1)

Figure 9:
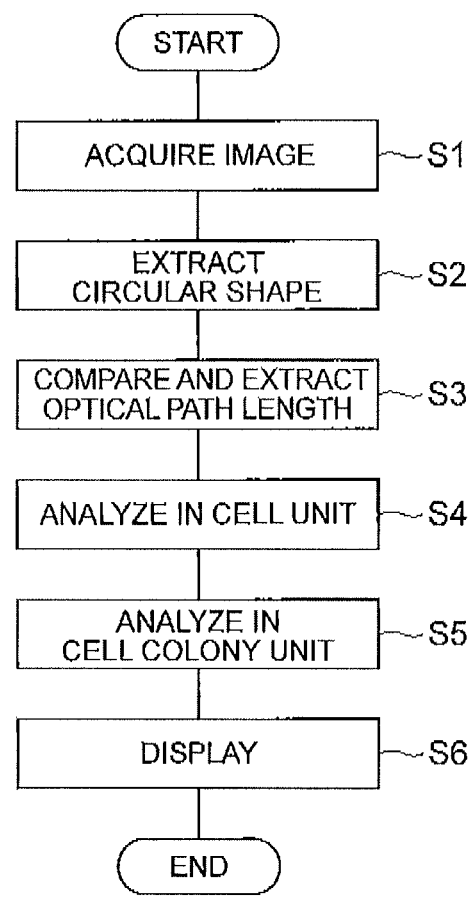
FIG. 9 is a flowchart illustrating operations performed by the cell analysis system 1.

Next, operations performed by the cell analysis system 1 configured as described above will be described in detail. FIG. 9 is a flowchart illustrating operations performed by the cell analysis system 1.

[Image Acquisition Process: Step S1]

First, the acquisition unit D1 acquires an optical path length image of a cell colony. The optical path length image of the cell colony is a quantitative optical path length image, and is obtained by imaging the output of the quantitative phase microscope A by the imaging device C, and outputting the image to the acquisition unit D1 of the cell analysis device D. Further, in the embodiment, the following operations will be described by using a stem cell as an example of a cell.

The quantitative optical path length image acquired in step S1 includes the following five types of cells. Further, the following "cell which is not a stem cell" refers to, for example, "a dead stem cell".

(a) stem cell with good quality
(b) stem cells with poor quality and having a circular shaped nucleus
(c) stem cells with poor quality and having a heteromorphic nucleus
(d) cells which are not a stem cell and have a circular shape
(e) cells which are not a stem cell and are heteromorphic

[Circular Shape Extraction Process: Step S2]

Next, the extraction unit D2 extracts circular shapes each corresponding to the cell nucleus of the cell in the acquired quantitative optical path length image. The extraction unit D2 may first specify a region of a stem cell colony from the quantitative optical path length image and then extract circular shapes each corresponding to the cell nucleus of each stem cell. During the extraction of circular shape, the circular shape may be extracted by first performing contour extraction as a pretreatment and then obtaining a portion with high turnout in the Hough transform with respect to the contour image. Hough transform is a method which is suitable for efficiently extracting a circular shape, but the present invention is not limited thereto, and may allow a circular shape to be extracted based on, for example, a curvature, and the like. The circular shape, which the extraction unit D2 extracts, may be a true circular shape, and the true circular shape may be a true circular shape with a diameter in a predetermined range (for example, approximately from 11 to 14 μm), or may be an elliptical shape.

By extracting a circular shape in step S2, the following three types of stem cells remain.

(a) stem cells with good quality
(b) stem cells with poor quality and having a circular shaped nucleus
(d) cells which are not a stem cell and have a circular shape

[Optical Path Length Comparison Extraction Process: Step S3]

Next, the comparison unit D3 compares an inner optical path length of the circular shape extracted in step S2 and an outer optical path length of the circular shape extracted in step S2. As a result of comparing the optical path lengths, the comparison unit D3 extracts one with a value of the optical path length in an outer region (a portion constituting the cytoplasm) of the circular shape which is greater than a value of the optical path length in an inner region (a portion constituting the cell nucleus) of the circular shape. Here, the comparison unit D3 may perform extraction using, as a determination criterion, the fact that an average value of the outer optical path lengths of the circular shapes is equal to or greater than a predetermined threshold as compared to an average value of the inner optical path lengths of the circular shapes. Alternatively, the comparison unit D3 may perform extraction using, as a determination criterion, the fact that a gradient of a horizontal and vertical profile, which is orthogonal to the circular shape, is a minus direction from the outer side to the inner side of the circular shape.

[Analysis Process 1, Analysis in Cell Unit: Step S4]

Next, the analysis unit D4 analyzes the circular shapes extracted in step S3 in cell unit. The analysis unit D4 determines that for the circular shape extracted in step S3, that is, extracted in step S2, when the outer optical path length thereof is greater than the inner optical path length thereof, the cell is a cell with good quality. This is because only (a) remains among the above (a), (b), and (d) in the extraction in step S3.

"Stem cells with poor quality and having a circular shaped nucleus" of the above (b) are excluded because a luminance difference between the inside and outside of the circular shape is not consistent with each other. The reason will be explained in the following. That is, the "optical path length", as represented in the following Equation (1), is obtained by multiplying the "physical thickness" by a "refractive index", and the difference in optical path length is expressed as a light-dark image with qualitativity in the quantitative optical path length image.

Optical path length=Refractive index×Physical thickness (1)

Here, as represented in the following Equation (2), it is generally known that the refractive index of the cell nucleus (inner side of the cell nucleus) is lower than that of the cytoplasm (outer side of the cell nucleus) (see, for example, the following Reference Literature 1).

Refractive index of the inner side of the cell nucleus<Refractive index of the outer side of the cell nucleus (2)

<References Literature 1>

Synthetic Aperture Tomographic Phase Microscopy for 3D Imaging of Live Cells In Translational Motion, Niyom Lue, Wonshik Choi, Gabriel Popescu, Kamran Badizadegan, Ramachandra R. Dasari, and Michael S. Feld, Optics Express, Vol. 16, Issue 20, pp. 16240-16246, 2008

Further, with respect to the physical thickness, in a stem cell with good quality, as represented in the following Equation (3), an inner physical thickness of the cell nucleus is almost the same as an outer physical thickness thereof. This is because in the stem cells with good quality, a distance between the adjacent stem cells is so close that the cytoplasm between the cell nuclei becomes thick.

(Stem Cells with Good Quality)

Inner physical thickness of the cell nucleus≈Outer physical thickness of the cell nucleus (3)

Meanwhile, in the a stem cell with poor quality, as represented in the following Equation (4), inner physical thickness of the cell nucleus is much thicker than outer physical thickness thereof. This is because in the stem cells with poor quality, a distance between the adjacent stem cells is so large that the cytoplasm between the cell nuclei becomes thin.

(Stem Cells with Poor Quality)

Inner physical thickness of the cell nucleus>>Outer physical thickness of the cell nucleus (4)

From the above, with respect to the stem cells with good quality, considering the relationship of Equations (2) and (3) in Equation (1), the following Equation (5) is established for the optical path length.

(Stem Cells with Good Quality)

Inner optical path length of the cell nucleus<Outer optical path length of the cell nucleus (5)

Meanwhile, with respect to stem cells with poor quality, considering the relationship of Equations (2) and (4) in Equation (1), the following Equation, (6) is established for the optical path length.

(Stem Cells with Poor Quality)

Inner optical path length of the cell nucleus>Outer optical path length of the cell nucleus (6)

Then, from the fact that the difference between the optical path lengths thereof is represented as light and shade information (luminance) with quantitativity in the quantitative optical path length image, when an inner luminance value of the cell nucleus is low and an outer luminance value of the cell nucleus is high in the quantitative optical path length image, that is, when the inner side of the nucleus appears dark, it can be said that the stem cell is a stem cell with good quality. Meanwhile, when an inner luminance value of the cell nucleus is high and an outer luminance value of the cell nucleus is low, that is, when the inner side of the nucleus does not appear dark, it can be said that the stem cells is a stem cell with poor quality.

For these reasons, as a result of comparing the optical path lengths in step S3, when the comparison unit D3 extracts one with a value of the optical path length in the outer region (portion constituting the cytoplasm) of the circular shape which is greater than the value of the optical path length in the inner region (portion constituting the cell nucleus) of the circular shape, it can be said that the extracted stem cell is a stem cell with good quality. That is, it can be said that "(b) stem cells with poor quality and having a circular shaped nucleus" are excluded by the extraction.

Further, in extraction in step S3, (d) "cells which are not a stem cell and have a circular shape" are also excluded because the differences in luminance of the inner and outer regions of the circular shape are not consistent with each other. The reason will be explained in the following. That is, cells considered as particles other than stem cells under the culture environment are mainly dead cells, and the refractive index of the dead cell is higher than that of the surrounding solution. Accordingly, the optical path length of the dead cell becomes a value higher than that of the surrounding, and an inner luminance value of the circular shape is high and an outer luminance value of the circular shape is low in the quantitative optical path length image, that is, the inner side of the circular shape appears brighter than the periphery thereof, and thus the dead cells are excluded by the extraction in step S3.

In addition, only the cell, which may not be excluded by the above method, is a case where a gap between stem cells is a circular shape by chance. The gaps make the refractive index lower than that of the periphery thereof and thus it is difficult to distinguish the stem cells as (a) "stem cells with good quality". However, these stem cells are not frequently found and does not cause any particular problem when a stem cell colony is analyzed using "the number of stem cells per unit area the quality of which are determined as being good" in the following determination in step S5.

[Analysis Process 2, Analysis in Cell Colony Unit: Step S5]

After the stem cells with good quality and the stem cells with poor quality are determined by the method in step S4 described above, when the number of the stem cells per unit area, which are determined as a stem cell with good quality, is equal to or greater than the threshold, the analysis unit D4 determines that the cell colony is a stem cell colony with good quality. Specifically, for example, when the density (ea/mm$^2$) of stem cells, which are determined as a stem cell with good quality, is equal to or greater than the threshold, the cell colony is determined as a stem cell colony with good quality.

Figure 10:
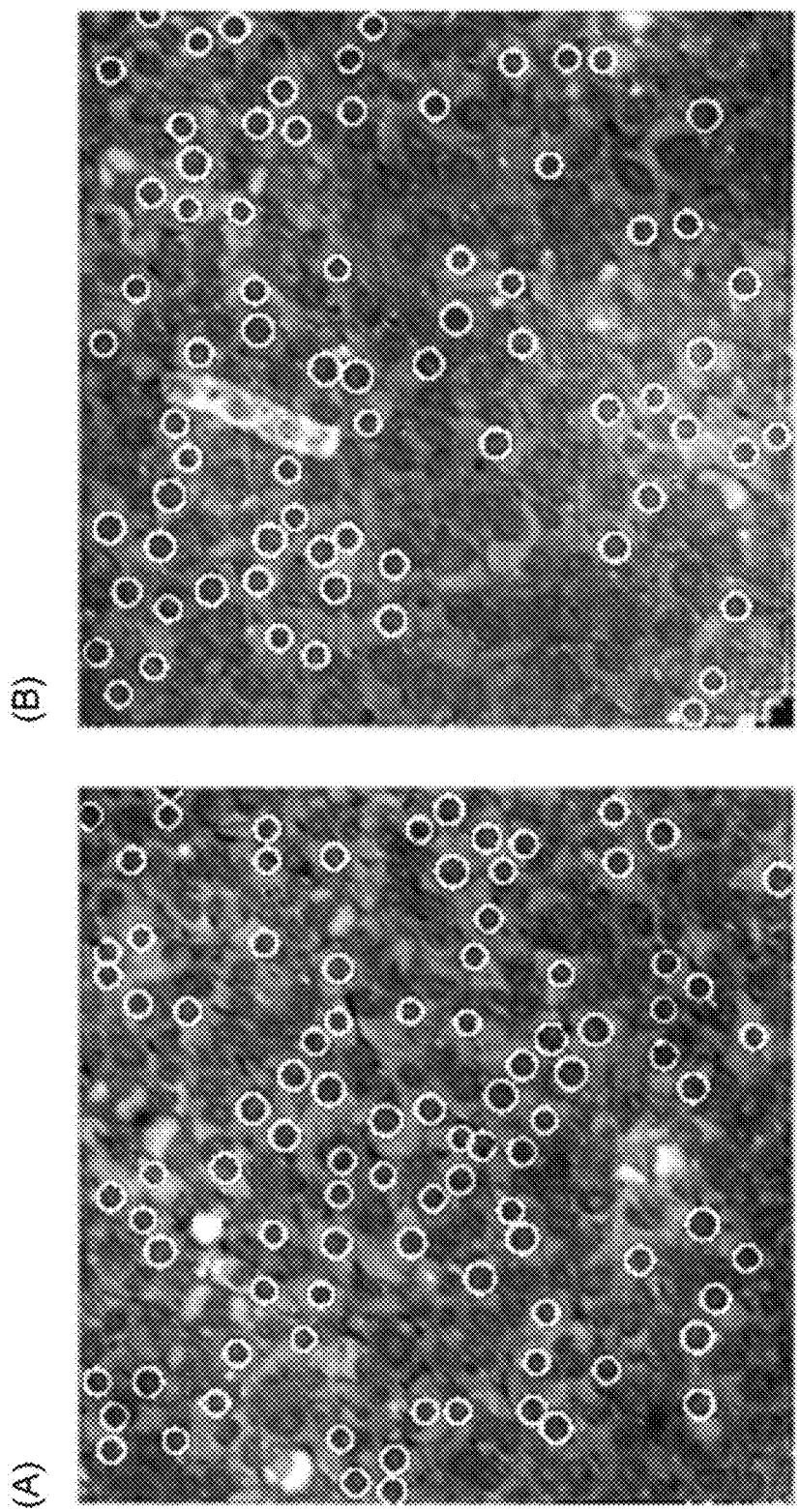
FIG. 10 is a view illustrating a cell colony the quality of which is determined as being good by a method in step S5 in FIG. 9.
Figure 11:
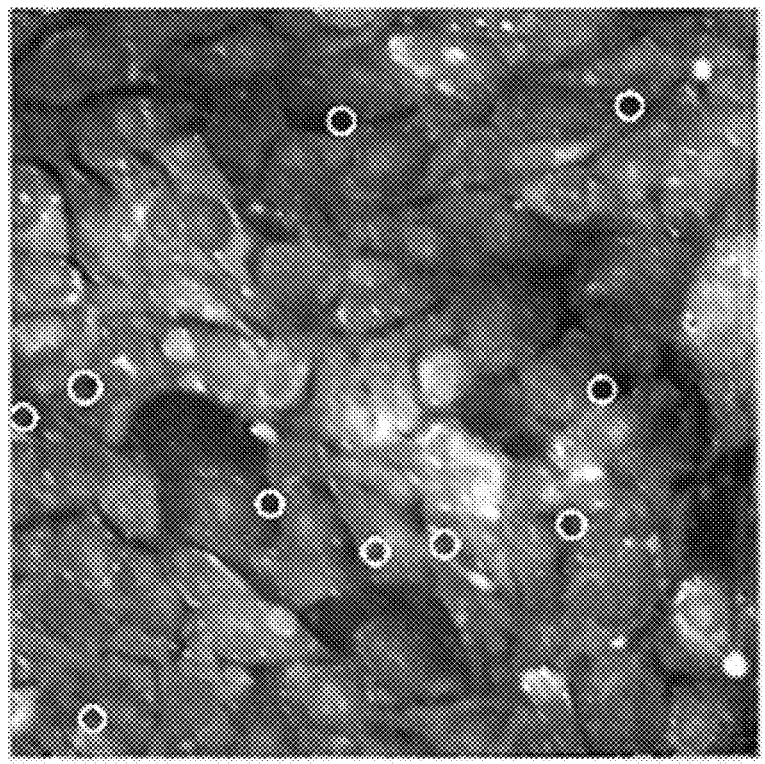
FIG. 11 is a view illustrating a cell colony the quality of which is determined as being poor by the method in step S5 in FIG. 9.
Figure 11:
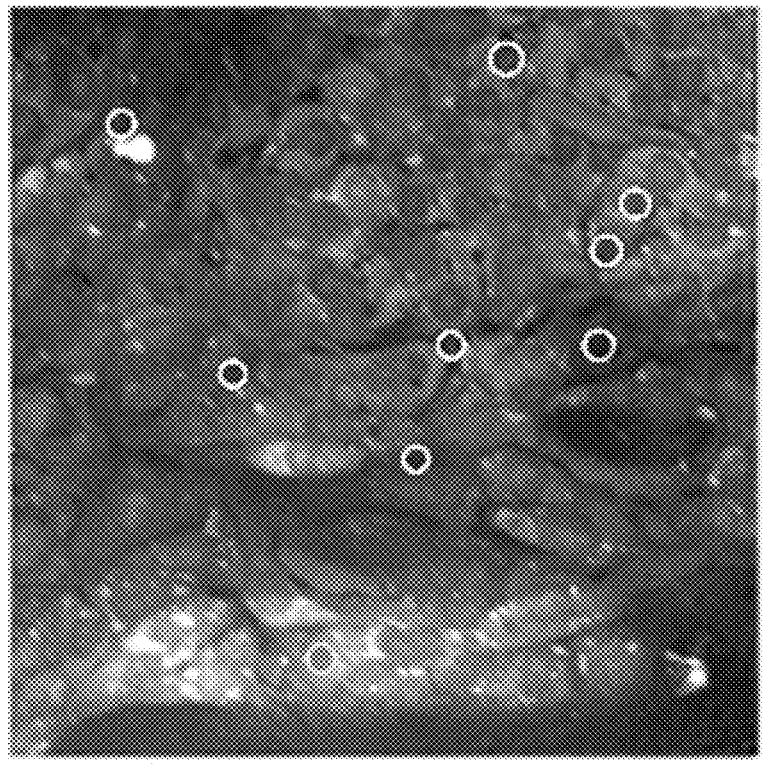
Figure 12:
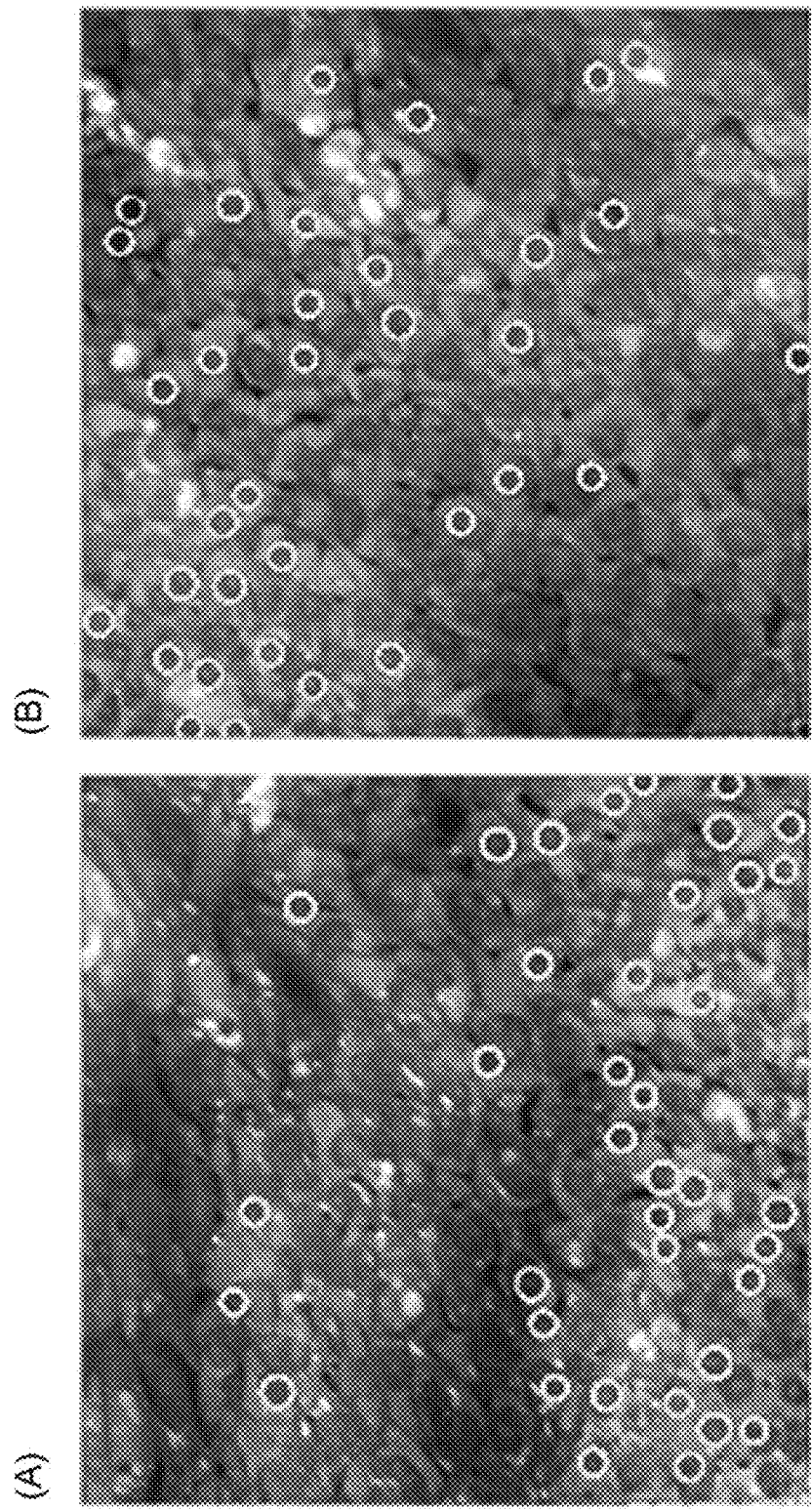
FIG. 12 is a view illustrating a cell colony in a case where a portion the quality of which is determined as being good and a portion the quality of which is determined as being poor coexist, by the method in step S5 in FIG. 9.

In each of FIGS. 10 to 12, (A) and (B) are views illustrating (a) "stem cells with good quality" extracted by the method described in the above step S4. In each drawing, the "stem cells with good quality" extracted in step S4 are indicated by a round and white solid line. FIG. 10 illustrates "stem cells with good quality" in a stem cell colony which is determined as a cell colony with good quality by the method in step S5, for example, from the fact that the density [ea/mm$^2$] of cells, which are determined as a cell with good quality is equal to or greater than the threshold. FIG. 11 illustrates "stem cells with good quality" in a stem cell colony which are determined as a cell colony with poor quality by the method in step S5. FIG. 12 illustrates "stem cells with good quality" in a case where a portion the quality of which is determined as being good and a portion the quality of which is determined as being poor coexist, by the method in step S5. In FIG. 12(A), an upper half thereof corresponds to the portion the quality of which is determined as being poor, and a lower half thereof corresponds to the portion the quality of which is determined as being good. In FIG. 12(B), an upper half thereof corresponds to the portion the quality of which is determined as being good, and a lower half thereof corresponds to the portion the quality of which is determined as being poor.

The processes of steps S2 to S4 may allow the analysis in the cell unit to be performed by extracting all the circular shapes and then comparing, the optical path lengths of each circular shape. Alternatively, the processes of steps S2 to S4 may also allow the analysis in the cell unit to be performed by repeating the process of extracting one circular shape and comparing, for the circular shape, the optical path lengths thereof.

[Display Process: Step S6]

Figure 13:
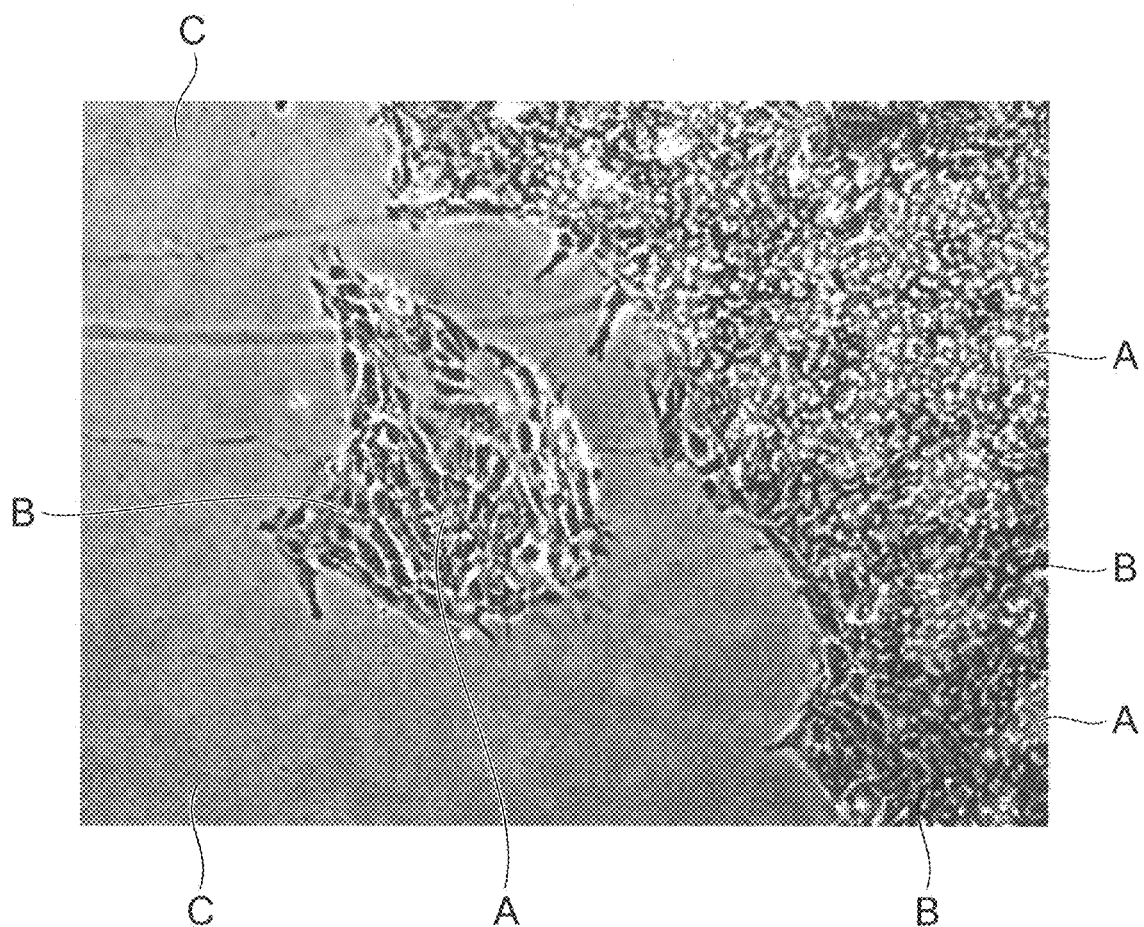
FIG. 13 is a view illustrating an example of a display by a display unit D5.

Next, the display unit D5 specifies and displays a region which is included in the stem cell colony the quality of which is determined as being good in step S5. FIG. 13 illustrates an example of a display by the display unit D5. In the example of FIG. 13, the display unit D5 performs a display by pseudo-color mapping. FIG. 13 illustrates the amount of information determined as stem cells with good quality (for example, true circular shapes extracted in steps S3 and S4) and the others distinguished from each other by shading. The amount of information determined as stem cells with good quality is present in the dark portion that is displayed by symbol A. Meanwhile, the amount of information determined as stem cells with poor quality is present in the light portion that is displayed by symbol B. Further, nothing is present in the portion that is displayed by symbol C. FIG. 13 is represented in color in the actually implemented aspect by the inventors, but it should be noted that FIG. 13, which is attached to the application in the application procedure, is a black and white drawing. In addition, the present applicant separately submits an actual color drawing of FIG. 13, for example, as a written statement. It is possible to grasp at a glance a two-dimensional distribution showing in which region of the stem cell colony the stem cells with good quality exist, by FIG. 13 as described above. That is, the left side of FIG. 13 is a portion which is determined as a region the quality of which is not good because a large number of stem cells with poor quality are present (symbol B). The right side of FIG. 13 is a portion which is determined as a region the quality of which is not good because a large number of stem cells with good quality are present (symbol A).

Figure 14:
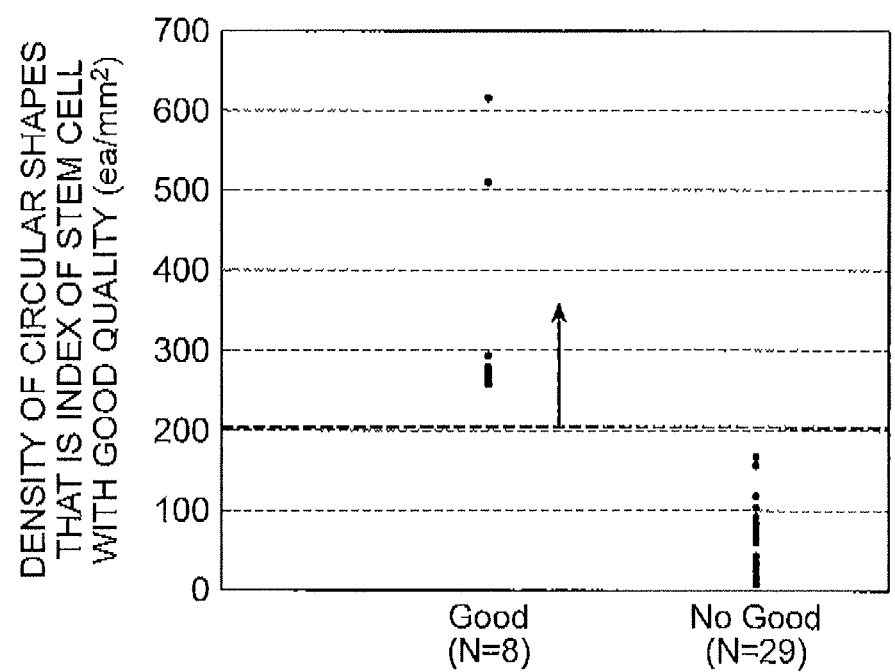
FIG. 14 is a view illustrating that the same results as the results through visual observation are obtained by the determination method in the embodiment.

FIG. 14 illustrates the density of the amount of information (for example, true circular shapes extracted in steps S3 and S4) determined as stem cells with good quality on the vertical axis and the result of determining the quality of stem cells by an observer's visual inspection along the horizontal axis. The amount of information in the samples (number of samples=8) the quality of which is determined as being good by visual inspection is represented by a point (Good) on the left side of FIG. 14, and the amount of information in the samples (number of samples=29) the quality of which is determined as being poor by visual inspection is represented by a point (No Good) on the right side thereof. As illustrated in FIG. 14, the determination method by the analysis unit D4 that determines a portion with a high density (for example, density 200 [ea/mm$^2$] or more) as a region with good quality coincides with the result of determining that the quality is good by visual inspection. That is, it can be said that a result, which is the same as the result by visual inspection, is obtained by the determination method in the embodiment.

Figure 15:
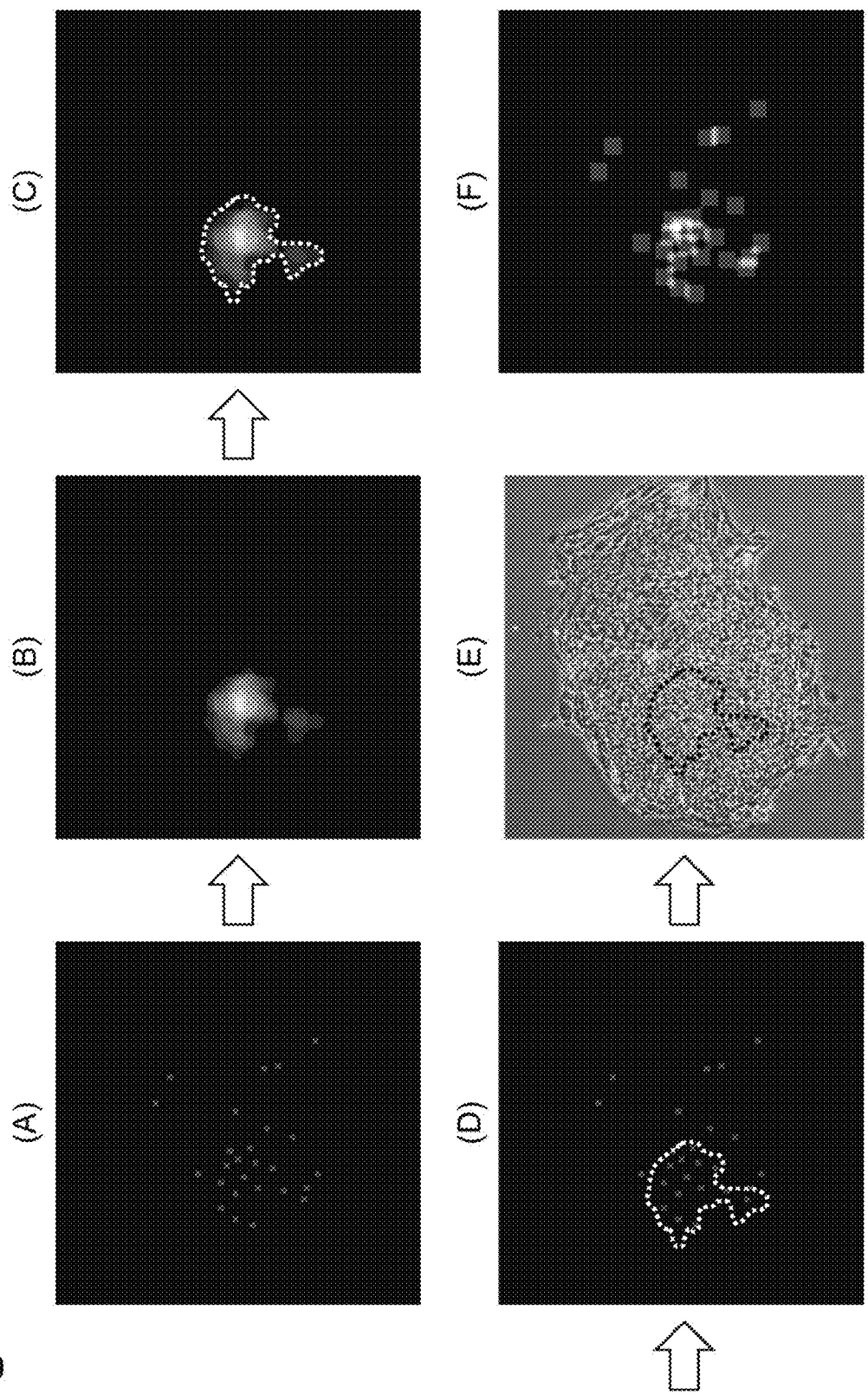
FIG. 15 is a view for explaining in detail operations by the display unit D5.

Hereinafter, the operations by the display unit D5 will be described in more detail. The operations of the display unit D5, which will be described below, relate to a method of displaying a stem cell colony (including some regions of the stem cell colony) with good quality using these densities when (a) "stem cells with good quality" are extracted via steps S2 to S4, and the "stem cells with good quality" are displayed, for example, by a round and white solid line in FIGS. 10 to 12. Hereinafter, (the operation will be described with reference to FIG. 15. Further, in the following description, a portion displayed by a round and white solid line in FIGS. 10 to 12 is defined as a "true circular object".

First, an image in which the true circular objects as in FIGS. 10 to 12 are displayed is inputted. Then, based on the inputted image, an image that displays a central coordinate of the true circular objects is created. FIG. 15(A) illustrates an image in which the central coordinate of the true circular objects is displayed. Further, the central coordinate of the true circular objects may be displayed, for example, by binarization and the like.

Next, a central coordinate (pixel) of a mask is substituted with the number of true circular objects, which are present in the mask, by preparing, for example, the rectangular mask with a suitable size with respect to the image illustrated in FIG. 15(A). The operation is performed on all the pixels while moving the mask. Further, the size of the mask is not particularly limited, but the gaps between the cells may not be filled when the size of the mask is too small. Accordingly, it is necessary to appropriately set a mask size in accordance with a distance between cells in the presence of cells, here, a distance between cell nuclei. For example, when the distance between cells is approximately 15 μm, it is also possible to use a mask having a diameter of 15 μm or more. Further, FIG. 15(F) illustrates an example that the size of the mask is so small that the operation does not properly work. In addition, from the viewpoint that the distance between the central coordinate is equally handled, the rectangular mask becomes a mask with a longer distance in a diagonal direction at 45 degrees, and thus a circular mask is more preferred than a rectangular mask.

Next, based on the number of true circular objects present in the mask that was substituted for the central coordinate of the mask as described above, a density image of a true circular objects having a distribution that the value increases according to the density of the true circular object is created. In the density image of the true circular objects, it is possible to exclude a low-density portion of the true circular objects by increasing the luminance value of the pixel depending on the density of the true circular objects. FIG. 15(B) illustrates the density image of the true circular objects created by the above method, and the high-density portion of true circular objects has a high luminance value and is displayed in white.

Next, with respect to the density image of the true circular objects illustrated in FIG. 15(B), the contour of the region is obtained using an appropriate threshold. In FIG. 15(C), the obtained contour is displayed as a broken line. Further, a region specified by the obtained contour coincides with a portion in which the density of the true circular objects is high, as illustrated in FIG. 15(D).

Next, the region specified by the contour in FIGS. 15(C) and (D) is aligned with the image of stem cell colony. Thus, in a region that specifies the stem cell colony, it is possible to specify and display a region the quality of which is good. FIG.

15(E) illustrates such an aspect, and a region surrounded and specified by a broken line is a region the quality of which is good in the stem cell colony. Further, from the image illustrated in FIG. 15(E), for example, information such as position coordinates may be retrieved and used in manipulation of cells (cut out and recovery).

Further, in the above operations, when the luminance values of the pixels of the density image of the true circular objects are increased in accordance with the density of the true circular objects (see FIG. 15(B)), and when the contour of the region is obtained using an appropriate threshold with respect to the density image of the true circular objects (see FIGS. 15(C) and (D)), it is possible to adjust the luminance values or to obtain the contour using, as a criterion, the fact that the objects are determined as a stem cell with good quality even by visual inspection in a case where the density of the true circular objects is 200 [ea/mm$^2$] or more. In addition, the fact that the density of the true circular objects is 200 [ea/mm$^2$] or more is also consistent with the result in FIG. 14 described above.

The operations by the display unit D5 described above are based on the concept described below. That is, cells form a cell colony while proliferating and thus have a strong tendency that cells having the same properties are adjacent to each other to form a cell population. That is, a large number of cells with good quality are present around cells with good quality, and thus when the true circular objects detected are present with a certain level of density, it may be determined that the region is formed of good cells. Due to the concept, it is possible to make a correct determination on the cell colony as a whole, for example, even though a little wrong determination is made on individual stem cells.

(Configuration Example of Cell Analysis Program)

The present invention may also be configured as a cell analysis program, and the foregoing description of the cell analysis device D may also be used as a description on the cell analysis program that causes a computer to function as the cell analysis device D. Overlapping description will be omitted, but the cell analysis program causes the computer to function as the acquisition unit D1, the extraction unit D2, the comparison unit D3, the analysis unit D4, and the display unit D5, which have been described above. The cell analysis program is provided by being stored in, for example, a recording medium. Further, as the recording medium, a recording medium such as a flexible disk, a CD, and a DVD, a recording medium such as an ROM, a semiconductor memory, and the like are exemplified.

(Operation and Effect of the Embodiment)

Hereinafter, the operation and effect of a cell analysis system 1 according to the embodiment will be described. According to the cell analysis system 1 of the embodiment, it is possible to analyze a stem cell colony with high accuracy by the quantitative and automated technique. That is, it is possible to analyze a cell colony with high accuracy by a quantitative and automated technique, by all including extracting a circular shape each corresponding to a cell nucleus of a stem cell and comparing an inner optical path length of the extracted circular shape and an outer optical path length of the extracted circular shape. By focusing on a difference between the inner and outer optical path lengths of the nucleus of the stem cell, that is, a difference between the optical path length in the nucleus of the stem cell and the optical path length in the cytoplasm around the nucleus of the stem cell, it is possible to use specific information of a stem cell with good quality for analysis of a stem cell colony, thereby analyzing a stem cell colony by a quantitative and automated technique. Further, it is possible to compensate for an appropriate analysis which was impossible with only extraction of a circular shape by focusing on not only shape information that the form is round, but also the quantitative difference in the optical path length, thereby realizing an analysis with high accuracy.

Further, in the above-described Patent Literature 3, since the inner brightness of the stem cell is compared with the outer brightness thereof, it is necessary to exactly extract the contour of the stem cell, but when stem cells forming a stem cell colony are adjacent to each other, a boundary between the stem cells is not clear, and thus it cannot be said that the contour of the stem cell may be extracted accurately. Meanwhile, the embodiment is different from Patent Literature 3 in that the inner and outer optical path lengths of the nucleus of the stem cell are compared with each other. Although a stem cell colony is formed, in a stem cell in good condition, the boundary of the nucleus of the stem cell may be clearly distinguished by a difference in refractive index between the nucleus and the cytoplasm thereof, and thus the inner and outer sides of the nucleus of the stem cell may be exactly distinguished. Therefore, according to the embodiment, it is possible to analyze a stem cell colony with high accuracy.

As described above, by analyzing a state of stem cell colony with high accuracy by the quantitative and automated technique, evaluation by experience of an examiner until now becomes numerical values, which may be objectively compared, even though the evaluation may be performed by anybody, and thus it is possible to exclude ambiguous factors such as a subjective view of an examiner, a physical condition thereof, and variability among examiners. This makes it possible to uniformly analyze a stem cell colony based on predetermined determination criteria that do not depend on the skill of the examiner. Further, it is possible to alleviate the physical pain of the examiner who observes and determines a large number of stem cells and stem cell colonies with naked eyes. In addition, for example, by applying stepwise numerical values, it is possible to understand a temporal change in state, and in this case, for example, after the initiation of culture, it is possible to determine the sign and the like that the state deteriorates early. For that reason, it is possible to increase an opportunity of recovery before a state deteriorates, improve the efficiency percentage in the entire process, and avoid wasting culture materials, thereby leading to a reduction in production costs. Furthermore, it is possible to easily apply the same determination criteria to a process of another producer, and provide stem cells with common quality among different producers.

Further, according to the embodiment, a specific method for determining a stem cell with good quality is provided. The determination method according to the embodiment is based on the following considerations by the inventors. That is, from the experimental results by the inventors, it has been derived that only in a stem cell with good quality, a shape of a nucleus of the stem cell is a circular shape and an inner optical path length of the nucleus is smaller than an outer optical path length of the nucleus. Meanwhile, it has been derived that in a stem cell with poor quality, a shape of a nucleus thereof is not a circular shape, or an inner optical path length of the nucleus is equal to or greater than an outer optical path length of the nucleus even though the shape of the nucleus is a circular shape. Therefore, it is possible to determine that a stem cell is a stem cell with good quality when an outer optical path length of a nucleus of the stem cell is larger than an inner optical path length of a nucleus by comparing the difference between the inner and outer optical path lengths thereof.

Further, according to the embodiment, a specific method for distinguishing between a stem cell colony with good quality and a stem cell colony with no good quality is provided. This is consistent with the purpose of industrial applications for quality management of a stem cell colony unit. It is because throughput does not increase by individually evaluating stem cells. In addition, the present method is a method based on the characteristics of a stem cell colony. That is, a stem cell colony is formed through division and proliferation of stem cells, and thus there is a tendency that there are a large number of stem cells with good quality around a stem cell with good quality, and there are a large number of stem cells with poor quality around a stem cell with poor quality. From this point of view, it can be said that the number of stem cells per unit area, which are determined as a stem cell with good quality, is appropriate as a determination criterion for distinguishing between a stem cell colony with good quality and a stem cell colony with no good quality Further, according to the embodiment, a specific method so as for a user to easily confirm the analysis result of a stem cell colony according to the embodiment is provided.

In addition, according to the embodiment, it is possible to readily compare an inner optical path length and an outer optical path length of a circular shape by a quantitative optical path length image.

Further, according to the embodiment, a primary determination criterion of a stem cell with good quality is provided. Depending on, for example, the accuracy or purpose of the stem cell analysis, it is possible to adopt as the determination criterion that the circular shape is a true circular shape In addition, it is possible to adopt as the determination criterion that the circular shape is a true circular shape having a predetermined diameter range. Alternatively, it is possible to adopt as the determination criterion that the circular shape is an elliptical shape.

The embodiment may be utilized in industrial applications of stem cells, including iPS stem cells and ES stem cells. For example, when the embodiment is applied to a device of culturing stem cells, and the like, it is possible to determine stem cells or stem cell colonies, which are being cultured, by a quantitative and automated technique and with higher accuracy, thereby enabling labor saving and mass production.

As described above, preferred embodiments of the present invention have been described, but it is obvious that the present invention is not limited to the above embodiments.

For example, in the above embodiment, in order to obtain an optical path length image of cells or cell colonies, a configuration in which the cell analysis system 1 includes the quantitative phase microscope A has been described as an example, but the present invention is not limited thereto, and for example, it is also possible to obtain an optical path length image of cells or cell colonies using a phase-contrast microscope. In this case, the device becomes inexpensive, thereby leading to cost savings.

REFERENCE SIGNS LIST

1 Cell analysis system
A Quantitative phase microscope
A1 Microscope main body
B Optical fiber
C Imaging device
D Cell analysis device
D1 Acquisition unit
D2 Extraction unit
D3 Comparison unit
D4 Analysis unit
D5 Display unit.

INDUSTRIAL APPLICABILITY

The present invention provides a cell analysis method, a cell analysis device, and a cell analysis program which may determine a state of a stem cell colony and which are quantitative and automated and with higher accuracy.

The invention claimed is:

1. A cell analysis method in a cell analysis device that uses a quantitative optical path length image of a cell colony formed of a number of cells to analyze the cell colony, the method comprising:
   acquiring the quantitative optical path length image of the cell colony by an acquisition unit of the cell analysis device;
   extracting a circular shape corresponding to a cell nucleus of a cell in the acquired quantitative optical path length image by an extraction unit of the cell analysis device;
   comparing an inner optical path length in an inner region of the extracted circular shape and an outer optical path length in an outer region of the extracted circular shape by a comparison unit of the cell analysis device; and
   analyzing the cell colony based on the comparison result by an analysis unit of the cell analysis device to identify a cell with good quality, wherein the outer optical path length of the circular shape is larger than the inner optical path length of the circular shape for the cell with good quality.

2. The cell analysis method according to claim 1, wherein in the analyzing, when a number of cells per unit, which are determined as the cell with good quality, is equal to or greater than a threshold, the cell colony is determined as a cell colony with good quality.

3. The cell analysis method according to claim 2, further comprising:
   specifying and displaying a region of the cell colony with good quality by display unit of the cell analysis device.

4. The cell analysis method according to claim 1, wherein the circular shape is a true circular shape.

5. The cell analysis method according to claim 4, wherein the true circular shape is a true circular shape having a predetermined diameter range.

6. The cell analysis method according to claim 1, wherein the circular shape is an elliptical shape.

7. The cell analysis method according to claim 1, wherein the cell is a stem cell.

8. A cell analysis system that uses a quantitative optical path length image of a cell colony formed of a number of cells to analyze the cell colony, the system comprising:
   a microscope, comprising:
     a stage that supports the cell colony; and
     a light emission source that irradiates light onto the cell colony mounted on the stage;
     an objective lens capable of viewing the irradiated cell colony on the stage;
     a camera that captures at least one image of at least a portion of the irradiated cell colony; and
   a cell analysis device, comprising:
     memory configured to store the at least one image captured by the camera;
     a processor communicatively coupled to the memory, the processor configured to:
       acquire the quantitative optical path length image of the cell colony;
       extract a circular shape corresponding to a cell nucleus of a cell in the acquired quantitative optical path length image;
       compare an inner optical path length in an inner region of the extracted circular shape and an outer optical path length in an outer region of the extracted circular shape; and analyze the cell colony based on the comparison result to identify a cell with good quality, wherein the outer optical path length of the circular shape is larger than the inner optical path length of the circular shape for the cell with good quality.

9. A non-transitory computer-readable medium containing program instructions for causing a computer to perform the method of:
in a cell analysis device that uses a quantitative optical path length image of a cell colony formed of a number of cells to analyze the cell colony, acquiring the quantitative optical path length image of the cell colony by an acquisition unit of the cell analysis device;
extracting a circular shape corresponding to a cell nucleus of a cell in the acquired quantitative optical path length image by an image extraction unit of the cell analysis device;
comparing an inner optical path length in an inner region of the extracted circular shape and an outer optical path length in an outer region of the extracted circular shape by a comparison unit of the cell analysis device; and
analyzing the cell colony based on the comparison result by an analysis unit of the cell analysis device to identify a cell with good quality, wherein the outer optical path length of the circular shape is larger than the inner optical path length of the circular shape for the cell with good quality.

10. A method for analyzing a cell based on quantitative optical path length image of the cell, the method comprising:
acquiring the optical path length image of the cell;
comparing a first quantitative optical path length of a first portion corresponding to a cell nucleus of the cell and a second quantitative optical path length of outside of the first portion;
and
determining that the cell is a cell with good quality based on the comparison result, wherein the second quantitative optical path length is larger than the first quantitative optical path length for the cell with good quality.

11. The method according to claim 10, further comprising: extracting a shape corresponding to the cell nucleus in the acquired quantitative optical path length image, wherein the first portion comprises an inside of the shape.

12. The method according to claim 10, wherein the outside of the first portion corresponds to a cytoplasm of the cell.

13. The method according to claim 10, wherein the cell is a stem cell.

14. The method according to claim 13, wherein the stem cell is an embryonic stem (ES) cell or an induced pluripotent stem (iPS) cell.

15. The method according to claim 10, wherein the cell is included in a cell colony.

16. The method according to claim 10, wherein each of the first quantitative optical path length and the second quantitative optical path length is a phase difference or an optical thickness.

17. The method according to claim 10, wherein the quantitative optical path length image is captured by using a phase contrast microscope or a quantitative phase microscope.

18. An apparatus for analyzing a cell based on a quantitative optical path length image of the cell, the apparatus comprising:
a computer including a processor and configured to:
acquire the quantitative optical path length image of the cell,
compare a first optical path length of a first portion corresponding to a cell nucleus of the cell and a second optical path length of outside of the first portion, and
determine that the cell is a cell with good quality based on the comparison result, wherein the second optical path length is larger than the first optical path length for the cell with good quality.

19. The apparatus according to claim 18, wherein the computer extracts a shape corresponding to the cell nucleus in the acquired quantitative optical path length image, and wherein the first portion comprises an inside of the shape.

20. The apparatus according to claim 18, wherein the outside of the first portion corresponds to a cytoplasm of the cell.

21. The apparatus according to claim 18, wherein the cell is a stem cell.

22. The apparatus according to claim 21, wherein the stem cell is an embryonic stem (ES) cell or an induced pluripotent stem (iPS) cell.

23. The apparatus according to claim 18, wherein the cell is included in a cell colony.

24. The method according to claim 18, wherein each of the first quantitative optical path length and the second quantitative optical path length is a phase difference or an optical thickness.

25. The apparatus according to claim 18, wherein the quantitative optical path length image is captured by using a phase contrast microscope or a quantitative phase microscope.

* * * * *